(12) United States Patent
Bloms-Funke et al.

(10) Patent No.: US 8,895,623 B2
(45) Date of Patent: Nov. 25, 2014

(54) INTRATHECAL OR EPIDURAL ADMINISTRATION OF 3-[(1S,2S)-3-(DIMETHYLAMINO)-1-ETHYL-2-METHYLPROPYL]PHENOL

(75) Inventors: Petra Bloms-Funke, Wuerselen (DE); Derek John Saunders, Aachen (DE); Eric Lang, Plainsboro, NJ (US)

(73) Assignee: Gruenenthal GmbH, Aachen (DE)

( * ) Notice: Subject to any disclaimer, the term of this patent is extended or adjusted under 35 U.S.C. 154(b) by 56 days.

(21) Appl. No.: 13/560,412

(22) Filed: Jul. 27, 2012

(65) Prior Publication Data

US 2013/0085184 A1    Apr. 4, 2013

Related U.S. Application Data

(60) Provisional application No. 61/513,163, filed on Jul. 29, 2011.

(51) Int. Cl.
*A61K 31/135* (2006.01)
*A01N 33/02* (2006.01)
*A61K 9/00* (2006.01)
*A61K 31/137* (2006.01)

(52) U.S. Cl.
CPC ............ *A61K 9/0085* (2013.01); *A61K 31/135* (2013.01); *A61K 31/137* (2013.01)
USPC ........................... 514/654; 514/649; 514/653

(58) Field of Classification Search
CPC ... A61K 31/135; A61K 31/137; A61K 45/06; A61K 9/0085
USPC .................... 514/646, 649, 653, 654
See application file for complete search history.

(56) References Cited

U.S. PATENT DOCUMENTS

| 6,248,737 | B1 * | 6/2001 | Buschmann et al. | 514/231.8 |
| 2005/0058706 | A1 | 3/2005 | Bartholomaeus et al. | |
| 2007/0254960 | A1 | 11/2007 | Bloms-Funke et al. | |
| 2010/0311842 | A1 | 12/2010 | Christoph et al. | |
| 2011/0098284 | A1 * | 4/2011 | Babul | 514/226.5 |
| 2011/0281855 | A1 * | 11/2011 | Sesha | 514/225.5 |

FOREIGN PATENT DOCUMENTS

| WO | WO 03/053427 A1 | 7/2003 |
| WO | WO 2012/119728 A1 | 9/2012 |

OTHER PUBLICATIONS

Tzschentke et al., "Tapentadol Hydrochloride", Drugs of the Future, 2006, vol. 31, No. 12, pp. 1053-1061 (nine (9) pages).
Collins et al., "Fentanyl Pharmacokinetics and Hemodynamic Effects in Preterm Infants during Ligation of Patent Ductus Arteriosus," Anesth. Analc., 1985, pp. 1078-1080, vol. 64, International Anesthesia Research Society.
Davis et al., "Opioids and Respiratory Depression," Drug Capsule, 1999, pp. 78-80, vol. 44, No. 1, Respiratory Care.
Lynn et al., "Morphine Pharmacokinetics in Early Infancy," Anesthesiology, 1987, vol. 66, pp. 136-139.
Purcell-Jones et al., "The use of opioids in neonates. A retrospective study of 933 cases," Anaesthesia, 1987, vol. 42, pp. 1316-1320.

* cited by examiner

*Primary Examiner* — My-Chau T Tran
(74) *Attorney, Agent, or Firm* — Crowell & Moring LLP

(57) ABSTRACT

The present invention relates to a method of providing pain management in a subject wherein the administration of the composition does not result in any non-central nervous system mediated systemic effect in the subject. In particular, the present invention relates to a method of administering 3-[(1S,2S)-3-(dimethylamino)-1-ethyl-2-methyl-propyl]-phenol in a space that is void of thrombocytes.

14 Claims, 1 Drawing Sheet

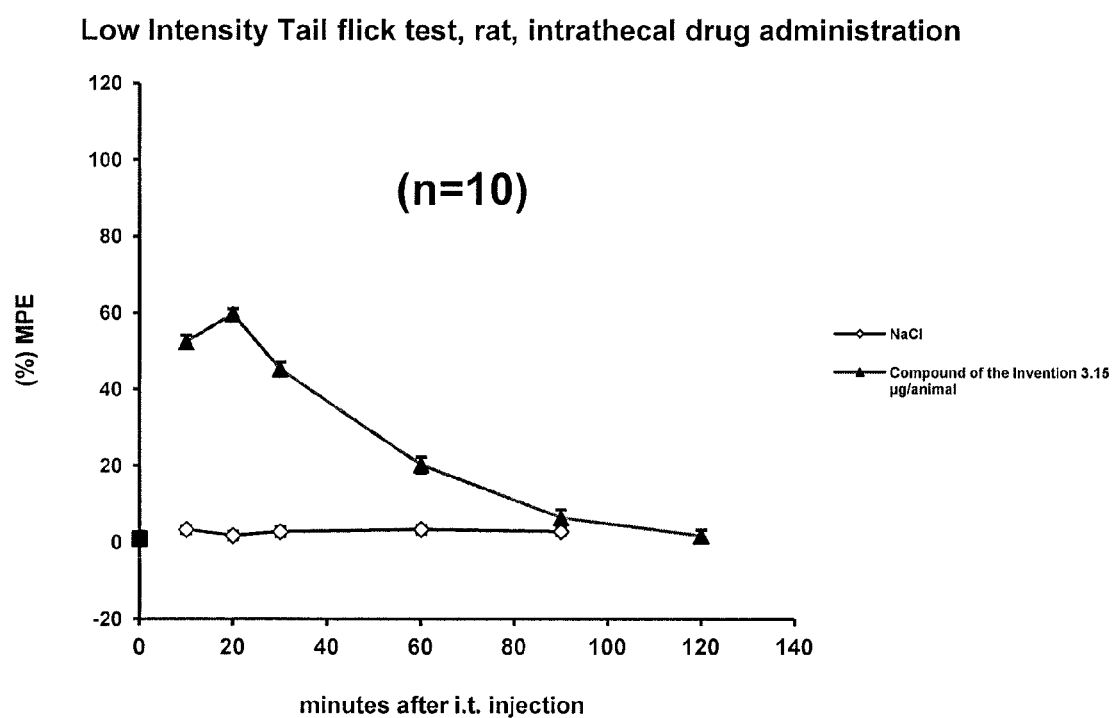

INTRATHECAL OR EPIDURAL ADMINISTRATION OF 3-[(1S,2S)-3-(DIMETHYLAMINO)-1-ETHYL-2-METHYLPROPYL]PHENOL

CROSS REFERENCE TO RELATED APPLICATIONS

This application claims priority from U.S. provisional patent application No. 61/513,163, filed Jul. 29, 2012, the entire disclosure of which is incorporated herein by reference.

FIELD OF THE INVENTION

The present invention relates to the intrathecal or epidural administration of 3-[(1S,2S)-3-(dimethylamino)-1-ethyl-2-methylpropyl]phenol for the treatment of pain.

BACKGROUND OF THE INVENTION

The treatment of acute and chronic pain is extremely important in medicine. There is currently a worldwide demand for additional highly effective pain treatment. The urgent need for action for patient-oriented and purposeful treatment of acute and chronic pain, this being taken to mean the successful and satisfactory treatment of pain for the patient, is documented in the large number of scientific papers which have recently appeared in the field of applied analgesics and fundamental research work on nociception.

Opioids have been used for many years as analgesics for the treatment of pain, however they give rise to a series of side effects, for example addiction and dependency, respiratory depression, gastrointestinal inhibition, nausea, vomiting, urinary retention and obstipation.

Millions of people suffer from pain. The pain may be minor, such as headaches, acute lower back pain, and acute muscle pain, or severe, such as chronic pain. Chronic pain may be associated with cancer treatment, HIV, diabetes, or other conditions. Chronic pain can be difficult to treat, with many chronic pain sufferers noting that their pain is not well controlled with current pain medications or that their medications have significant associated adverse effects (for example, nausea and vomiting, dependence, tolerance, etc.). Chronic pain is pain that extends beyond the expected period of healing. Acute pain generally is of limited duration and subsides quickly again after removal of the stimulus triggering it.

One problem in combating chronic and acute pain are the side-effects, in particular respiratory depression, of μ-opioids, such as morphine or fentanyl, which are highly effective against chronic and acute pain. Unfortunately, it is often not possible to effectively treat pain without opioids. Therefore, because of the fear of respiratory depression and further side-effects typical of μ-opioids in many cases this results in opioids being used to an inadequate extent in severe pain, for example in cancer patients (Davis et al., Respiratory Care Journal 1999, 44 (1)).

In an attempt to address the problem of chronic pain management, intrathecal and epidural infusion pumps and catheters have been developed. These modalities are aimed at intermittent, continuous, or near continuous delivery of a variety of liquid analgesic agents which include opioids, local anesthetics and drugs with other mechanisms. Many infusion pumps are totally implantable, which helps to reduce the risk of infection when compared to the long-term use of external systems. The infusion pump may also be programmable to allow patients or their clinicians to adjust dosing amounts or daily delivery schedule, helping to meet a patient's changing needs.

Epidural or intrathecal delivery of opioids has the advantage that it is likely to decrease the incidence of opioid side effects that are mediated through peripheral or supraspinal mechanisms (e.g. obstipation, GI dysfunction, components of nausea and vomiting, potentially components of urinary retention etc.). Despite this intent no opioid, to date, has been restricted to the central nervous system thereby eliminating the possibility that peripherally mediated opioid side effects might occur.

During childbirth, many women receive combinations of local anesthetic and opioids to prevent the pain associated with childbirth via epidural catheter. The process of inserting the epidural catheter can on occasion inadvertently cannulate an epidural blood vessel which can lead to an unintentional systemic administration of the intended epidural solution.

The use of opioids in young infants requires special consideration and expertise. Newborn infants, especially premature babies or those who have neurologic abnormalities or pulmonary disease, are susceptible to apnea and respiratory depression when systemic opioids are used (Purcell-Jones et al., The use of opioids in neonates. A retrospective study of 933 cases. *Anaesthesia* 1987; 42(12):1316-20). The infant's metabolism is altered so that the elimination half-life is longer and the blood-brain barrier is more permeable (Collins et al., Fentanyl pharmacokinetics and hemodynamic effects in preterm infants during ligation of patent ductus arteriosus. Anesth Analg. 1985; 64(11):1078-80; Lynn et al., Morphine pharmacokinetics in early infancy. *Anesthesiology* 1987; 66(2):136-9). Both factors result in young infants having higher in-brain concentrations of opioids for a given dose than do mature infants or adults. Inadvertent maternal systemic exposure to opioids during the delivery process can lead to respiratory depression and the need for resuscitation of the newborn infant.

There is thus an urgent need for new medicaments for the treatment of pain, that limit the side effects associated with opioids and offer the potential of greater safety where newborn infants are involved.

SUMMARY OF THE INVENTION

The object of the present invention is to provide a method of providing opioid analgesia to a subject wherein the administration of the composition does not result in any peripherally or supraspinally mediated side effect in the subject.

It has surprisingly been found that 3-[(1S,2S)-3-(dimethylamino)-1-ethyl-2-methyl-propyl]phenol or a physiologically acceptable salt thereof is unexpectedly particularly effective in locally treating or inhibiting pain in a subject without exhibiting any peripherally or supraspinally mediated side effects in the subject.

Accordingly, the invention relates to a method of locally treating or inhibiting pain in a subject in need thereof, comprising administering to said subject in a space that is void of thrombocytes, a pharmacologically effective amount of 3-[(1S,2S)-3-(dimethylamino)-1-ethyl-2-methyl-propyl]phenol or a physiologically acceptable salt thereof, whereby said administration does not result in any peripheral or supraspinal side-effect in the subject.

This object is further achieved according to the invention by providing a composition comprising 3-[(1S,2S)-3-(dimethylamino)-1-ethyl-2-methylpropyl]-phenol which has a specific analgesic effect in the epidural and intrathecal space of a subject. This compound can be used to locally treat or inhibit pain, in particular chronic and/or non-chronic pain, and even more particularly, severe chronic pain requiring implantable permanent or temporary catheters which includes cancer pain or pain associated with childbirth where epidural or intrathecal opioid is administered.

This object is further achieved by providing a method of administering the composition of the present invention comprising 3-[(1S,2S)-3-(dimethylamino)-1-ethyl-2-methyl-propyl]phenol into the intrathecal or epidural space of a subject.

This object is further achieved by administering into the epidural or intrathecal space of the subject a dose selected from the group consisting of a single bolus dose, an intermittent bolus dose and a continuous infusion dose.

This object can be achieved by administering the composition using an intrathecal or epidural pump or an intrathecal or epidural catheter. This object can also be achieved by using a permanent or temporary catheter. Also, this object can be achieved by using an implantable pump.

Additionally, this object can be achieved by administering the composition by a single bolus dose, intermittent bolus doses or continuous infusion.

BRIEF DESCRIPTION OF THE DRAWINGS

FIG. 1 shows a representation of the efficacy of 3-[(1S,2S)-3-(dimethylamino)-1-ethyl-2-methylpropyl]phenol as compared to a vehicle control group in a low intensity tail flick test in rats after intrathecal drug administration.

DETAILED DESCRIPTION

Tapentadol, i.e. (-)-(1R,2R)-3-(3-dimethylamino-1-ethyl-2-methyl-propyl)-phenol, is a synthetic, centrally acting analgesic which is effective in the treatment of moderate to severe, acute or chronic pain.

It has surprisingly been found that the enantiomer of tapentadol, (3-[(1S,2S)-3-(dimethylamino)-1-ethyl-2-methyl-propyl]phenol) has a unique bioavailability. (3-[(1S,2S)-3-(dimethylamino)-1-ethyl-2-methylpropyl]phenol) has a potency similar to that of fentanyl, and it has been shown that this compound induces antinociceptive effects after local injection into the spinal cord in an animal model of acute pain (see Example 2). However, it has surprisingly been found that 3-[(1S,2S)-3-(dimethylamino)-1-ethyl-2-methyl-propyl] phenol has no relevant oral bioavailability or intravenous bioavailability in humans because the compound is rapidly metabolized in the blood of humans by very rapid uptake and sulphation that occurs in blood thrombocytes.

This unique bioavailability provides useful characteristics in a variety of clinical situations. In particular, this compound is useful for treating subjects who are not able to take oral opioids, and require intrathecal or epidural opioid administration. For example, during childbirth, women often receive epidural or intrathecal opioids alone, or in combination with a local anesthetic. Opioids administered this way can inadvertently be absorbed systemically through the incorrect placement of the epidural catheter, or by using lipid soluble opioids like fentanyl or sufentanil that are more prone to leak into the maternal systemic circulation and can thus be transferred trans-placentally to the infant during delivery. In rare cases, this can lead to respiratory depression in the infant, which requires resuscitation of the infant. Another example of a clinical situation in which this unique bioavailability would be useful is in subjects receiving opioid treatments through epidural catheters or implanted intrathecal pumps for severe chronic pain or cancer pain. Subjects receiving this type of treatment are typically thus treated to decrease the incidence of peripherally or supraspinally mediated opioid side effects such as obstipation, GI dysfunction, components of nausea and vomiting, potentially components of urinary retention etc.

By using the compound of the present invention, the side effects resulting from the opioid entering the blood stream would be mitigated or eliminated entirely. Once the compound enters the blood stream, the compound is rapidly sulphated by thrombocytes and is therefore inactivated. Because the cerebrospinal fluid (CSF) and the epidural space are free of thrombocytes, the compound remains available for action in these spaces.

Suitable for the administration of 3-[(1S,2S)-3-(dimethylamino)-1-ethyl-2-methyl-propyl]phenol are also spaces with no or minor metabolism by thrombocytes.

Accordingly, the different embodiments of the invention as described herein also relate to the use of 3-[(1S,2S)-3-(dimethylamino)-1-ethyl-2-methyl-propyl]phenol or a physiologically acceptable salt thereof in spaces with no or minor metabolism by thrombocytes.

Until now, no existing opioid has been reported that is thus restricted after local administration to the epidural or intrathecal space.

In summary, local epidural or intrathecal administration together with lack of systemic bioavailability offer the option of effective pain treatment without typical systemic, peripherally or supraspinally mediated, opioid side effects such as respiratory depression, addiction, dependency, nausea, vomitus, constipation/obstipation, and urinary retention.

In addition, the method offers a treatment option with no trans-placentally exposure during delivery and ensures safety of the newborn child.

3-[(1S,2S)-3-(dimethylamino)-1-ethyl-2-methylpropyl] phenol, can be made using the method described in U.S. Pat. No. 6,248,737, the entire disclosure of which is hereby incorporated by reference.

The pharmaceutical composition of the present invention can be formulated for administration to a subject via various routes. The term "subject" as used herein can be a mammal, for example a human, or a patient. The term "subject in need thereof", as used herein, is for example a mammal in need of pain relief, a human in need of pain relief, or a patient in need of pain relief. The pharmaceutical composition of the present invention can be formulated for administration to a subject via any route that introduces the composition into a space void of thrombocytes. For example, administration can be made in the intrathecal, epidural or intracerebroventricular spaces.

The pharmaceutical composition of the present invention can be administered intrathecally by continuous infusion such as with a catheter, or a pump, or intrathecally by a single bolus injection or by intermittent bolus injection. Additionally, the pharmaceutical composition of the present invention can be administered epidurally by continuous infusion such as with a catheter, or a pump, or by a single bolus injection or by intermittent bolus injection.

As used herein, the terms "intermittent bolus injection" or "intermittent bolus dose" include, for example, the administration of the pharmaceutical composition to the subject more than one time but not continuously. This intermittent administration can be for example, administration of the pharmaceutical composition every thirty minutes, every hour, every few hours, every several hours, every day, or every couple of days, or combinations thereof.

When the pharmaceutical composition of the present invention is administered by continuous infusion, implantable delivery devices, such as an implantable pump may be employed. Examples of delivery devices that can be used within the scope of the invention include devices which can be implanted subcutaneously in the body or on the cranium, and provides an access port through which therapeutic agents may be delivered to the nerves or brain. Delivery occurs through an implanted catheter. The infusion pump may be an intrathecal pump, an epidural delivery infusion pump, or a patient control analgesia pump.

The pharmaceutical composition of the present invention is advantageously administered in the form of a substantially pure stereoisomer, in particular, enantiomer or diastereomer, or in the form of a mixture of the stereoisomers containing predominantly the 1S,2S enantiomers or diastereomers.

Depending upon the formulation, the pharmaceutical composition of the invention preferably contains suitable additives and/or excipients. Suitable additives and/or excipients for the purpose of the invention include all such substances for the preparation of galenic formulations known to persons skilled in the art. The selection of these excipients and the amounts to be used depend upon how the pharmaceutical composition is to be administered, as well as on the weight and condition of the subject and can readily be determined by a person of ordinary skill by routine experimentation.

Examples of suitable additives and/or excipients include water, buffered saline, ethanol, polyol (for example, glycerol, propylene glycol, liquid polyethylene glycol and the like), dimethyl sulfoxide (DMSO), oils, injectable organic esters, such as ethyl oleate, detergents, preservatives, wetting agents, emulsifying agents, dispersing agents, suspending agents or suitable mixtures thereof. Furthermore, this compound can be administered in combination with local anesthetics or other analgesics suitable for administration in the epidural or intrathecal space.

The amount of active ingredient to be administered to the subject varies depending on the weight of the subject, on the type of administration, the indication being treated, and on the severity of the pain.

The active ingredient can be formulated for administration in a one dose bolus injection, in a continuous infusion, or as a single dose to be intermittently administered throughout the course of treatment. Methods of determining the most effective means and dosage of administration are well known to those of skill in the art and vary with the composition used for therapy, the purpose of the therapy, and the subject being treated. Single or multiple administrations are carried out with the dose level and pattern being selected by the treating physician.

When the active ingredient is formulated for administration in a single dose, i.e., a bolus injection, or as a dose to be administered intermittently throughout the course of treatment, normally less than 1 mg, preferably less than 500 µg, and particularly preferably less than 250 µg of the active ingredient is administered per kg of subject body weight.

When the active ingredient is formulated for administration as a continuous infusion, normally less than 250 µg per kg of subject body weight is administered per hour, more preferably, less than 125 µg per kg of subject body weight is administered per hour, and even more preferably, less than 75 µg per kg of subject body weight is administered per hour.

EXAMPLES

The following examples are provided in order to demonstrate and further illustrate certain preferred embodiments and aspects of the present invention and are not to be construed as limiting the scope thereof.

Example 1

Pharmacokinetic profile of 3-[(1S,2S)-3-(dimethylamino)-1-ethyl-2-methyl-propyl]phenol The probability of different routes of metabolic clearance in vivo can be investigated by estimating the rates of the underlying oxidation or conjugation reactions in vitro using sub-cellular fractions such as hepatic microsomes. Because the rate of microsomal oxidation of 3-[(1S,2S)-3-(dimethylamino)-1-ethyl-2-methylpropyl]phenol could be shown to be very low, it was considered that oxidative metabolism was unlikely to be a significant metabolic clearance route for this molecule. A similarly low rate of microsomal oxidation was also demonstrated for the enantiomeric antipode of 3-[(1S,2S)-3-(dimethylamino)-1-ethyl-2-methylpropyl]phenol (hereinafter 3-[(1R,2R)-3-(dimethylamino)-1-ethyl-2-methylpropyl]phenol).

The principal route of metabolic clearance of 3-[(1R,2R)-3-(dimethylamino)-1-ethyl-2-methylpropyl]phenol in most species, including humans, is glucuronidation, and this route was therefore considered to be very likely to be dominant for 3-[(1S,2S)-3-(dimethylamino)-1-ethyl-2-methylpropyl]phenol as well. Indeed, in vitro investigations showed that the rates of glucuronidation of the two enantiomers were very similar. Consequently, as the oral bioavailability of 3-[(1R,2R)-3-(dimethylamino)-1-ethyl-2-methyl-propyl]phenol in humans was known to be ca. 33%, it was expected that the oral bioavailability of 3-[(1S,2S)-3-(dimethylamino)-1-ethyl-2-methylpropyl]phenol in humans would be similar. Surprisingly, the oral bioavailability of 3-[(1S,2S)-3-(dimethylamino)-1-ethyl-2-methylpropyl]phenol was effectively zero.

On examination of the pharmacokinetics of the two compounds after intravenous administration, it became clear that the rate of elimination of 3-[(1S,2S)-3-(dimethylamino)-1-ethyl-2-methylpropyl]phenol was much higher than that of 3-[(1R,2R)-3-(dimethylamino)-1-ethyl-2-methylpropyl]phenol, and higher even than could be explained on clearance of the total hepatic blood flow. The elimination halftime of 3-[(1R,2R)-3-(dimethylamino)-1-ethyl-2-methylpropyl]phenol in humans is ca. 3.2 h; if the clearance of 3-[(1S,2S)-3-(dimethylamino)-1-ethyl-2-methylpropyl]phenol was limited by the liver blood flow, an elimination halftime of 2.2 h would be expected. In fact, the elimination halftime of 3-[(1S,2S)-3-(dimethylamino)-1-ethyl-2-methylpropyl]phenol was ca. 0.75 h.

After intravenous administrations of equal doses, the initial plasma concentrations of 3-[(1S,2S)-3-(dimethylamino)-1-ethyl-2-methylpropyl]phenol and 3-[(1R,2R)-3-(dimethylamino)-1-ethyl-2-methylpropyl]phenol are essentially identical, proving that the two enantiomers distribute similarly. Consequently, the short elimination halftime of 3-[(1S,2S)-3-(dimethylamino)-1-ethyl-2-methylpropyl]phenol can be explained only if its clearance occurs at 5-fold the hepatic blood flow, indicating that supplementary, presumably non-hepatic, clearance route(s) are involved.

Clearances of the order of cardiac output could result from extensive metabolism in the lung as the complete cardiac output passes this organ. However, as there are no known lung-specific metabolic clearance routes which could be expected to apply more to 3-[(1S,2S)-3-(dimethylamino)-1- ethyl-2-methylpropyl]phenol than to 3-[(1R,2R)-3-(dimethylamino)-1-ethyl-2-methyl-propyl]phenol, this appeared to be an unlikely explanation.

The remaining possibility was that the high clearance was due to a stereo-selective biochemical process occurring in blood itself. If true, then it would be expected that 3-[(1S,2S)-3-(dimethylamino)-1-ethyl-2-methylpropyl]phenol, but not 3-[(1R,2R)-3-(dimethylamino)-1-ethyl-2-methylpropyl]phenol, would be metabolised in a time-, concentration-, and temperature-dependent manner by whole human blood.

To test the hypothesis, blood was withdrawn from healthy volunteers, heparinised (final heparin concentration, 15 U/ml), and spiked with 1 µM 3-[(1S,2S)-3-(dimethylamino)-1-ethyl-2-methylpropyl]phenol or 3-[(1R,2R)-3-(dimethylamino)-1-ethyl-2-methylpropyl]phenol. It was mixed on a rotary mixer at 37° C. in closed test-tubes. The rate of loss of the added compounds was determined by taking aliquots at regular intervals, centrifuging at 5000 g for 5 minutes, and analysing the supernatant.

Supernatants were alkalinized by addition of aqueous 25% ammonia (50 µl/ml plasma), spiked with an internal standard, and extracted twice with tertiary butyl methyl ether (2 ml per ml plasma). The ether layers were combined and dried in a stream of nitrogen before being reconstituted in 150 µl chromatography buffer (see below).

All assay supernatants were analysed by reversed-phase HPLC on a Inertsil 5 ODS 2 column (250×4.6 mm). The HPLC system consisted of equipment from Dionex or Gynkotek. The auto-sampler was a GINA 50T unit (Gynkotek); the pump system was type P580A LPG (Gynkotek); the column was thermostatted at 30° C. using a SHT 585 unit (Gynkotek). Effluents were generally monitored for fluorescence emission at 300 nm after excitation at 215 nm using a RF 2000 detector (Dionex); the wavelengths for excitation and emission were chosen to be optimal for 3-[(1S,2S)-3-(dimethylamino)-1-ethyl-2-methylpropyl]phenol or 3-[(1R,2R)-3-(dimethylamino)-1-ethyl-2-methylpropyl]-phenol. Chromatograms were evaluated using Chromeleon software version 6.11 (Dionex).

Generally, the samples were eluted using an isocratic solvent mixture. Sodium pentane-sulphonate was dissolved at 1.92 g/l (10 mM)=PSS; perchloric acid (PA) was 60% w/v. A mixture containing 900 ml PSS, 210 ml methanol, 80 ml tetrahydrofuran, and 0.1 ml PA was made, allowed to stand overnight, and degassed prior to passage over the column. The effluent was passed first through the UV detector, and then into the fluorescence detector.

No loss of 3-[(1R,2R)-3-(dimethylamino)-1-ethyl-2-methylpropyl]phenol was observed. In contrast, a linear loss of 35% of the added 3-[(1S,2S)-3-(dimethylamino)-1-ethyl-2-methylpropyl]phenol was observed over the course of one hour. This value is very close to the supplementary loss of 50%/h (in addition to the expected glucuronidation rate) needed to explain the human in vivo clearance. When the same experiment was conducted at room temperature (24° C.), a loss of only 7% was observed; and at 6° C., no loss was observed. Evidently the involved process was temperature-dependent.

At concentrations in excess of 1 µM 3-[(1S,2S)-3-(dimethylamino)-1-ethyl-2-methylpropyl]phenol, net losses in whole blood were sub-linear, suggesting that the clearance process was enzymatic and evidently saturable at concentrations above 2 µM—though not at pharmacologically relevant concentrations (<1 µM). Blood consists of plasma, plasma enzymes, and various blood cell types (erythrocytes, leukocytes, thrombocytes etc). 3-[(1S,2S)-3-(dimethylamino)-1-ethyl-2-methylpropyl]phenol was expected, and proven, to be stable to plasma. Of the blood cell types, thrombocytes (platelets) were expected to have the highest relevant enzymatic activity in SULT1A3, a sulphotransferase.

Thrombocyte (platelet-)enriched plasma can be prepared by centrifuging blood at 400 g for 10 minutes as this precipitates larger cells (erythrocytes, leukocytes). Incubation in the thrombocyte-enriched plasma won from a given volume of blood was able to cause the loss of an amount of 3-[(1S,2S)-3-(dimethylamino)-1-ethyl-2-methylpropyl]phenol (but not of 3-[(1R,2R)-3-(dimethylamino)-1-ethyl-2-methylpropyl]phenol) equivalent to that observed on incubation in the original volume of whole blood in a time-, concentration-, and temperature-dependent fashion, suggesting that the losses were caused by thrombocytes only. From the concentration dependency of the reaction rate, the Km of the process was estimated to be 3.5 µM. After incubation of 14C-3-[(1S,2S)-3-(dimethylamino)-1-ethyl-2-methylpropyl]phenol with whole blood or thrombocyte-enriched plasma, only a single reaction product was observed, and this eluted identically on HLPC to synthetic 3-[(1S,2S)-3-(dimethylamino)-1-ethyl-2-methylpropyl]phenol-sulphate.

Thrombocyte sulphotransferase SULT1A3 conjugates and thereby inactivates systemic biogenic amines (dopamine, noradrenaline, serotonin). These biogenic amines are transported into the thrombocytes by specific transporters which can be inhibited by a variety of compounds. It was shown that the rate of conjugation of 3-[(1S,2S)-3-(dimethylamino)-1-ethyl-2-methylpropyl]phenol was influenced neither by inhibitors of dopamine transport (cocaine, 10 µM; nomifensin, 10 µM; amphetamine, 100 µM) nor inhibitors of noradrenaline transport (fluoxetine, 10 µM), nor inhibitors of serotonin transport (desipramine, 100 µM). In addition, no accumulation of 3-[(1S,2S)-3-(dimethylamino)-1-ethyl-2-methylpropyl]phenol-sulphate was observed in pelleted thrombocytes under any condition. Consequently, import of 3-[(1S,2S)-3-(dimethylamino)-1-ethyl-2-methylpropyl]phenol into the cells, nor export of the conjugated metabolite, appears to require the assistance of any of these transporters.

As no accumulation of 3-[(1S,2S)-3-(dimethylamino)-1-ethyl-2-methylpropyl]phenol-sulphate was observed in thrombocytes, it is unlikely that it could affect thrombocyte function. As the Km of the reaction (3.5 µM) is well above physiologically relevant concentrations (<1 µM), the rate of sulphation will be linearly related to the 3-[(1S,2S)-3-(dimethylamino)-1-ethyl-2-methylpropyl]phenol concentration. In addition, it will be proportional to the thrombocyte count in blood. This is typically $1.5\text{-}3.0*10^5$ cells/µl, but may be reduced 10-fold in thrombocytopenia; this can occur in bone-marrow diseases, after cytostatic or radio-therapy, or on treatment with diuretics, penicillins or streptomycin. In subjects with extreme thrombopenia, it can be assumed that metabolic clearance of 3-[(1S,2S)-3-(dimethylamino)-1-ethyl-2-methylpropyl]-phenol will occur predominantly by glucuronidation at a rate equivalent to that observed for 3-[(1R,2R)-3-(dimethylamino)-1-ethyl-2-methylpropyl]phenol, increasing the halftime of elimination from 0.75 h to ca. 3 h.

In conclusion, 3-[(1S,2S)-3-(dimethylamino)-1-ethyl-2-methylpropyl]phenol is cleared by a novel route, sulphation by thrombocytes. This guarantees that its rate of clearance is very high, which would prevent it accumulating systemically to concentrations at which it could evoke general central pharmacological effects. Thus if applied locally, especially in at a low dose rate, it is likely that only local pharmacological effects will occur.

Example 2

Efficacy of 3-[(1S,2S)-3-(dimethylamino)-1-ethyl-2-methylpropyl]phenol after Intrathecal Drug Administration in an Animal Model for Acute Nociceptive Pain Antinociceptive effects of 3-[(1S,2S)-3-(dimethylamino)-1-ethyl-2-methylpropyl]-phenol were evaluated in the low intensity tail-flick test after local drug application into the spinal cord of rats.

Material and Methods:

Animals 160 male Sprague Dawley rats (200 to 260 g body weight) from a commercial breeder (Janvier, Le Genest St Isle, France) were housed under standardized conditions: light/dark rhythm (06.00-18.00 h light, 18.00-06.00 h dark); room temperature 20-24° C.; relative air humidity 35-70%; 15 air changes per hour, air movement <0.2 m/sec. The animals were given water and feedstuff designed for rats/mice/hamsters from Nohrlin (Bad Salzuflen, FRG) ad libitum. They were kept in groups of six in Makrolon cages type 4. There were at least 5 days between the day of delivery and the day of testing.

Experimental Preparation

The experiments were performed using a Tail-flick device from Rhema-Labortechnik (Hofheim/Ts., FRG). Before and after drug application, a radiant heat beam was focused onto the dorsal surface of the rat's tail about 2 to 4 cm apart from the root. During the test, the animals were restrained. The latency from switching on the lamp to tail withdrawal was measured. The intensity of the radiant heat beam was adjusted to 40% of the maximum value so that a mean pre-test value of 4.5-9 sec was obtained for each animal group. Only animals which showed both pre-test latencies of 15 sec or lower, and whose pre-test values did not differ by more than 2 sec, were used for testing. To avoid tissue damage, the radiant heat beam was switched off at the latest after 30 sec if the tail was not withdrawn. The animals were tested 10, 20, 30, 60, 90 and 120 min p. appl. Intrathecal administrations of 3-[(1S,2S)-3-(dimethylamino)-1-ethyl-2-methylpropyl]phenol were performed under light ether anesthesia, by injecting between L1 and L3. A control group was treated with 0.9% saline.

Data Analysis

The individual latencies were calculated as the percentage of the Maximum Possible Effect (% MPE) according to the following formula:

$$\% \text{ MPE} = (\text{latency} - VTM)/(30\text{sec} - VTM) * 100\%$$

VTM: mean pre-test value, 30 sec: cut off value.

Data were expressed as mean±s.e.m. of the respective animal group.

Results

After intrathecal (i.t.) administration of 3.15 μg/animal, 3-[(1S,2S)-3-(dimethylamino)-1-ethyl-2-methylpropyl]phenol induced an antinociceptive effect which was long-lasting and reached a maximum of 59.71±2.94% MPE 20 min p. appl. as shown in FIG. 1.

Tail withdrawal latencies are expressed as percentage of maximum possible effect (% MPE). Control animals were injected i.t. with saline. Data are expressed as mean±s.e.m. (n=10).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method of locally treating or inhibiting pain in a subject in need thereof comprising administering to said subject, in a space that is void of thrombocytes, a therapeutically effective amount of a composition comprising 3-[(1S,2S)-3-(dimethylamino)-1-ethyl-2-methylpropyl]phenol or a physiologically acceptable salt thereof, whereby administration of said composition does not result in any peripherally or supraspinally mediated side effect in the subject.

2. The method of claim 1, wherein said subject is a human.

3. The method of claim 1, wherein said composition is administered into the intrathecal space of the subject.

4. The method of claim 3, wherein said composition is administered by an intrathecal pump.

5. The method of claim 4, wherein said pump is implanted in the subject.

6. The method of claim 1, wherein said composition is administered in the epidural space of the subject.

7. The method of claim 6, wherein said composition is administered via an epidural catheter.

8. The method of claim 7, wherein said epidural catheter is a permanent or temporary catheter.

9. The method of claim 6, wherein said composition is administered by a pump.

10. The method of claim 1, wherein said pain being treated is pain associated with childbirth.

11. The method of claim 1, wherein said pain being treated is chronic pain or cancer pain.

12. The method of claim 1, wherein the composition is administered into the epidural or intrathecal space of the subject by a dose selected from the group consisting of a single bolus dose, an intermittent bolus dose and a continuous infusion dose.

13. The method of claim 3, wherein the composition is administered in combination with one or more other drugs that are suitable for administration in the intrathecal space.

14. The method of claim 6, wherein the composition is administered in combination with one or more other drugs that are suitable for administration in the epidural space.

* * * * *